United States Patent
Hsieh et al.

(10) Patent No.: US 7,646,842 B2
(45) Date of Patent: Jan. 12, 2010

(54) METHODS AND APPARATUS FOR RECONSTRUCTING THICK IMAGE SLICES

(75) Inventors: Jiang Hsieh, Brookfield, WI (US); Xiangyang Tang, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 45 days.

(21) Appl. No.: 11/233,670

(22) Filed: Sep. 23, 2005

(65) Prior Publication Data

US 2007/0071159 A1 Mar. 29, 2007

(51) Int. Cl.
*A61B 6/00* (2006.01)

(52) U.S. Cl. .......................................... 378/4

(58) Field of Classification Search ............... 378/4–21, 378/210, 901
See application file for complete search history.

(56) References Cited

U.S. PATENT DOCUMENTS

| | | | | |
|---|---|---|---|---|
| 5,406,479 A * | 4/1995 | Harman | | 378/7 |
| 5,473,654 A | 12/1995 | Kotian et al. | | |
| 5,825,842 A | 10/1998 | Taguchi | | |
| 5,828,718 A * | 10/1998 | Ruth et al. | | 378/19 |
| 5,881,122 A * | 3/1999 | Crawford et al. | | 378/4 |
| 6,118,841 A * | 9/2000 | Lai | | 378/19 |
| 6,137,856 A | 10/2000 | Lin | | |
| 6,240,157 B1 * | 5/2001 | Danielsson | | 378/15 |
| 6,343,108 B1 * | 1/2002 | Heuscher | | 378/4 |
| 6,415,013 B1 | 7/2002 | Hsieh et al. | | |
| 6,438,201 B1 * | 8/2002 | Mazess et al. | | 378/56 |
| 6,477,221 B1 * | 11/2002 | Ning | | 378/4 |
| 6,529,575 B1 * | 3/2003 | Hsieh | | 378/4 |
| 6,587,537 B1 * | 7/2003 | Hsieh | | 378/4 |
| 6,724,856 B2 | 4/2004 | De Man et al. | | |
| 6,771,732 B2 * | 8/2004 | Xiao et al. | | 378/4 |
| 6,795,522 B2 | 9/2004 | Nishide et al. | | |
| 6,873,679 B2 | 3/2005 | Hagiwara | | |
| 6,885,764 B2 | 4/2005 | Wang et al. | | |
| 7,006,591 B2 | 2/2006 | Machida | | |
| 7,203,268 B2 | 4/2007 | Yahata | | |
| 2003/0091143 A1 * | 5/2003 | Grass et al. | | 378/42 |
| 2003/0206609 A1 * | 11/2003 | Kling et al. | | 378/4 |

* cited by examiner

*Primary Examiner*—Edward J Glick
*Assistant Examiner*—Alexander H Taningco
(74) *Attorney, Agent, or Firm*—Armstrong Teasdale LLP

(57) ABSTRACT

A method for obtaining data includes scanning an object using a CT imaging system having at least two detector rows to acquire projection data, wherein the projection data includes at least some data obtained from at least two rows of the detector array, and reconstructing data representative an image of the object utilizing the projection data wherein the reconstruction includes pipelining the acquired projection data through a pipeline of operations including column-filtering, tomographic filtering, and backprojection. Thick reconstructed images using 3D backprojection can be obtained with significantly lessened artifacts relative to conventional 3D backprojection image reconstructions.

20 Claims, 8 Drawing Sheets

METHODS AND APPARATUS FOR RECONSTRUCTING THICK IMAGE SLICES

BACKGROUND OF THE INVENTION

This invention relates generally to reconstruction of computed tomographic (CT) images, and more particularly to generation of thick image slices utilizing 3D backprojection.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

For moderate cone beam angles, artifacts produced by FDK-type reconstructions are adequately suppressed. With the increased volume coverage enabled by known multi-slice CT detectors, however, cone beam related image artifacts can no longer be ignored. Because of the 3D-backprojection process used in FDK-type reconstructions, the z-filtering technique used in 2D approximations does not necessarily provide adequate results. To fully understand the issue, a 2D z-filtering technique used in at least one known CT imaging apparatus is described.

Let us denote by $w'(\gamma, \beta, n)$ the weighting function for a projection sample at detector channel $\gamma$, view angle $\beta$, and detector row n. The weighted projection, $p'(\gamma, \beta, n)$, is then written:

$$p'(\gamma,\beta,n)=w'(\gamma,\beta,n)p(\gamma,\beta,n). \qquad (1)$$

In equation (1), the weighting function can be obtained by convolving the weighting function in the "native mode" (in which no slice broadening is intended), $w(\gamma, \beta, n)$, with a z-filter function, $f(\beta)$ (because $\beta$ is linearly related to z):

$$w'(\gamma,\beta,n)=w(\gamma,\beta,n)\otimes f(\beta) \qquad (2)$$

Because the cone angle is ignored, the multiple detector rows and view angles are summed to produce a single 2D sinogram, $s(\gamma, \beta)$:

$$s(\gamma, \beta) = \sum_{\forall \beta'=\beta\pm 2\pi} \sum_{n=1}^{N} p'(\gamma, \beta, n). \qquad (3)$$

For any reconstruction method that employs 3D backprojection (such as FDK-type reconstructions), the difference between the samples collected from different detector rows cannot be ignored, since the row location becomes reconstruction pixel dependent. Consequently, this formulation is no longer valid and the resulting artifacts can be significant.

More particularly, in at least one known method of reconstruction and referring to FIG. 8, for a given source trajectory 80, x-rays will pass from a moving source 14 through an object (not shown) and onto a multirow detector array 18. A weighted and filtered backprojection is back-projected in 3D so that each backprojection path 802 corresponds to an x-ray path (i.e., pixel-driven backprojection rays) that generated the projection sample. Because each detector element (individual detector elements are not shown in FIG. 6) has a finite size (and also a finite width and height), rays 802 cast from each pixel will not, in general, always land on a center of a detector row 804. For this reason, at least one known 3D backprojection method uses linear interpolation between measured samples to arrive at an interpolated sample for reconstruction.

Some of the samples used in this reconstruction are obtained by contributions from two detector rows and some are obtained with a single detector row. The relative contribution from the two rows also depends on the relative row location with respect to the intersection point. In helical mode, the interpolation occurs in a periodic fashion and leads to a periodic artifact pattern when the scanned object changes quickly in z, as shown in the prior art reconstruction of FIG. 9.

BRIEF DESCRIPTION OF THE INVENTION

In one aspect, some configurations of the present invention therefore provide a method for obtaining data. The method includes scanning an object using a CT imaging system having at least two detector rows to acquire projection data, wherein the projection data includes at least some data obtained from at least two rows of the detector array. The method further includes reconstructing data representative an image of the object utilizing the projection data wherein the reconstruction includes pipelining the acquired projection data through a pipeline of operations including column-filtering, tomographic filtering, and backprojection.

In another aspect, some configurations of the present invention provide a CT imaging apparatus having a detector array with at least two rows and a plurality of columns, and a radiation source configured to project a beam of radiation through an object to be imaged onto the detector array. The CT imaging apparatus is configured to scan an object to acquire projection data, wherein the projection data includes at least some data obtained from at least two rows of the detector array. The CT imaging apparatus is further configured to reconstruct data representative an image of the object utilizing the projection data. The reconstruction includes pipelining the acquired projection data through a pipeline of operations including column-filtering, tomographic filtering, and backprojection.

In yet another aspect, some configurations of the present invention provide a medium having recorded thereon machine-readable instructions configured to instruct a processor to input projection data, and to reconstruct data representative of an image of the object utilizing the projection data. The reconstruction includes instructions to pipeline the acquired projection data through a pipeline of operations including column-filtering, tomographic filtering, and backprojection. The instructions on the medium are further configured to instruct the processor to produce an image of the object on a display screen utilizing the data representative of the image of the object.

It will thus be appreciated that various configurations of the present invention provide thick 3D backprojection with reduced artifacts relative to images reconstructed with known techniques.

DETAILED DESCRIPTION OF THE INVENTION

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
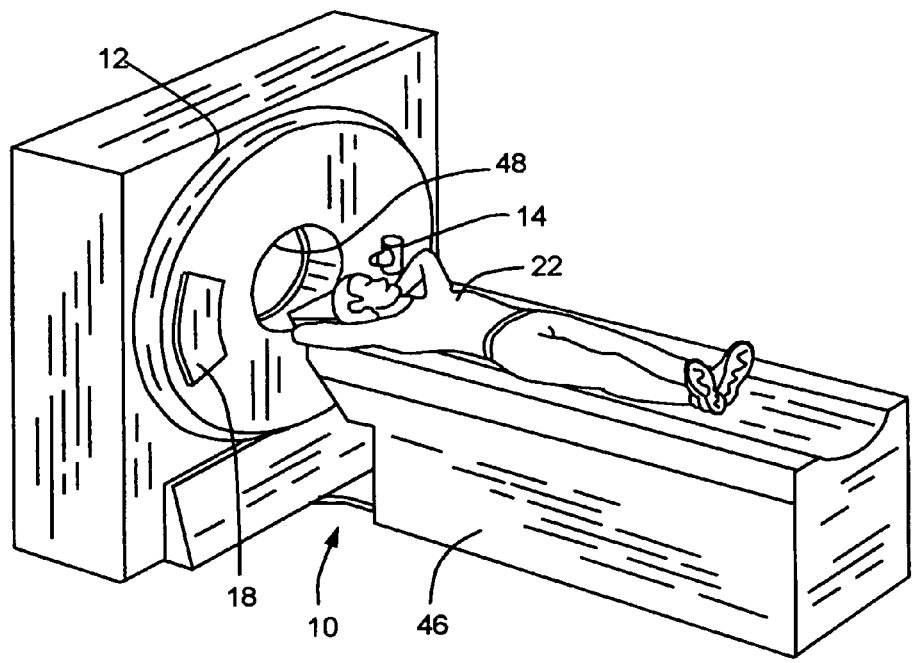
FIG. 1 is a pictorial. diagram representative of some configurations of CT imaging systems of the present invention.
Figure 2:
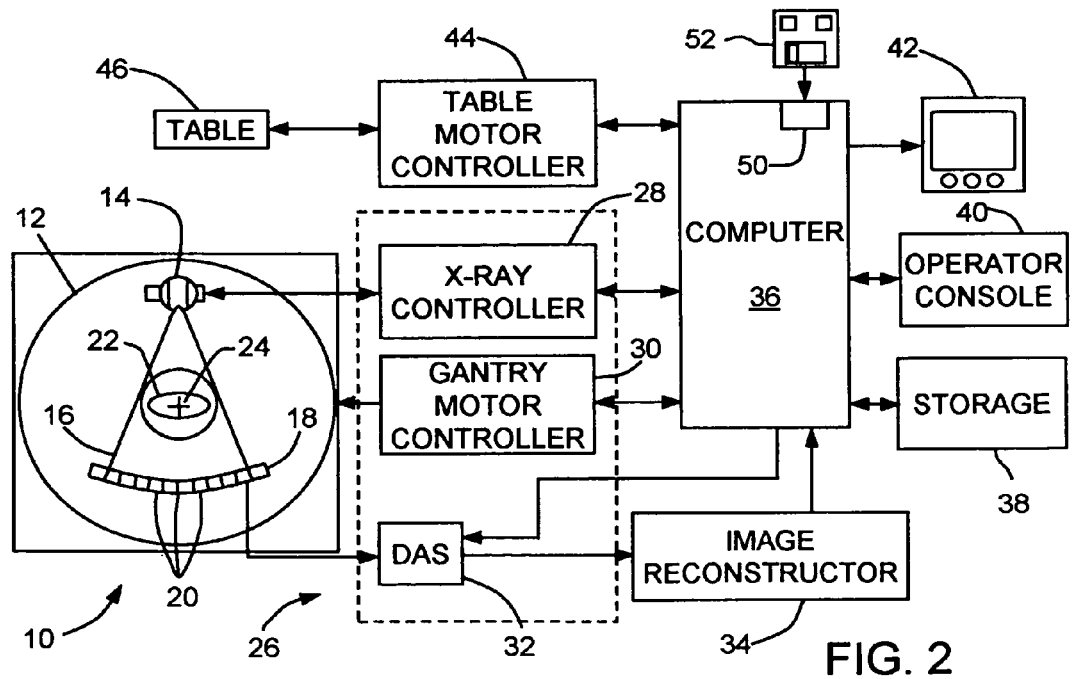
FIG. 2 is a functional block diagram of the CT imaging system of FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36. It will be understood that the block diagram of FIG. 2 is closer to a logical representation of the functions described herein than a physical block diagram. Particular hardware and/or firmware and/or software implementations of these functions can be left as a design choice to one or more people skilled in the art of logic and/or computational circuit design and/or computer programming upon such person(s) gaining an understanding of the principles of the present invention presented herein.

Computer 36 also receives commands and scanning parameters from an operator via console 40 that has a keyboard. An associated cathode ray tube display (CRT), liquid crystal display (LCD), plasma display or other suitable visual display device 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, or a DVD. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector-rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 3:
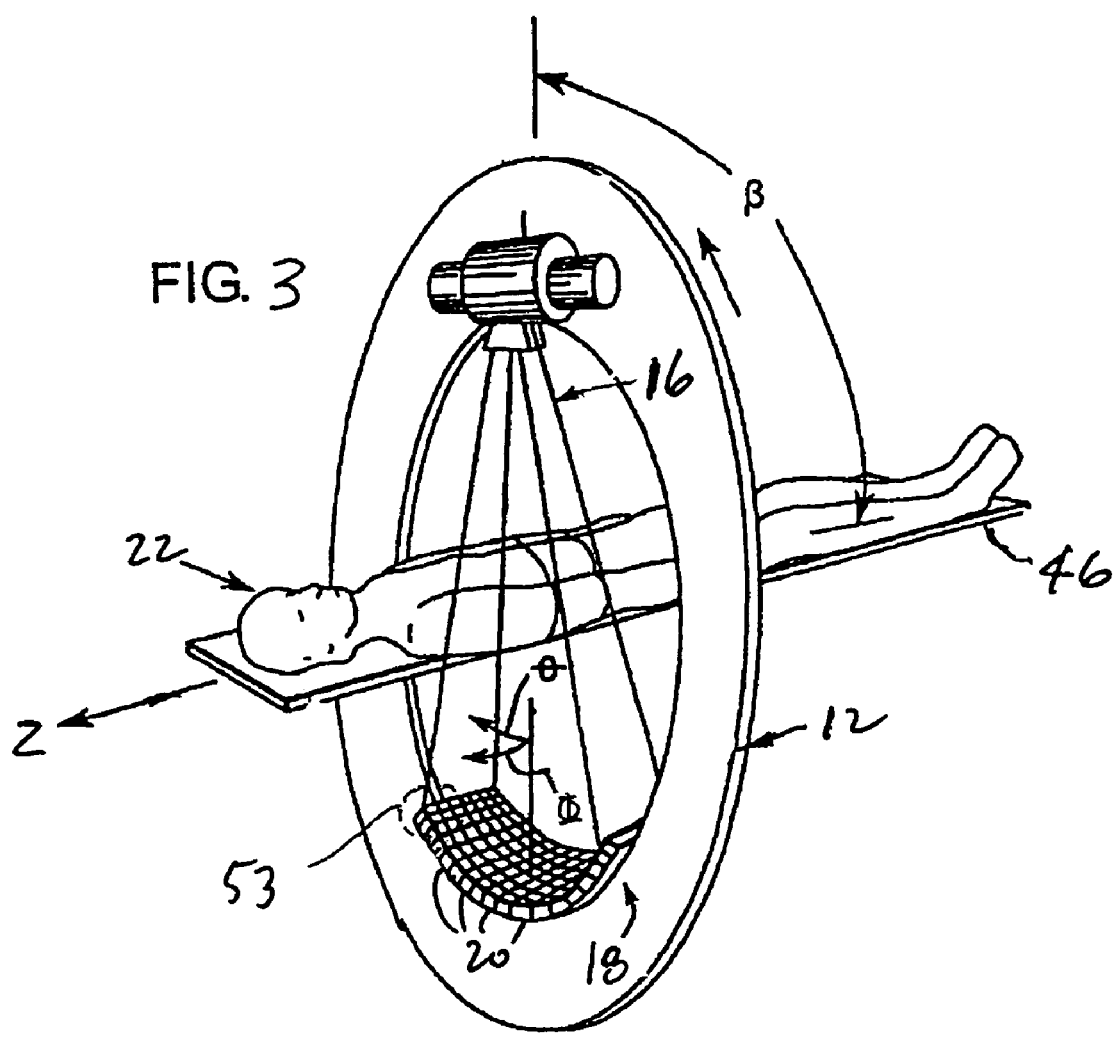
FIG. 3 is pictorial diagram showing some of the components of the CT imaging system of FIG. 1, and in particular, showing the orientation of the multi-row detector array and certain angles of interest.

In some configurations and referring to FIG. 3, detector array 18 is a multirow detector array. Radiation source 14 and multirow detector array 18 are mounted on opposing sides of gantry 12 so that both rotate about an axis of rotation. The axis of rotation forms the z-axis of a Cartesian coordinate system having its origin centered within x-ray beam 16. The plane defined by the "x" and "y" axes of this coordinate system thus defines a plane of rotation, specifically the plane of gantry 12.

Rotation of gantry 12 is measured by an angle β from arbitrary reference position within plane of gantry 20. Angle β varies between 0 and 2π radians. X-ray beam 16 diverges from the gantry plane by an angle Φ and diverges along the gantry plane by angle Θ. Detector array 18 has a generally arcuate cross-sectional shape and its array of detector elements 20 are arranged to receive and make intensity measurements along the rays of x-ray beam 16 throughout the angles of Φ and Φ of radiation beam 16.

Figure 4:
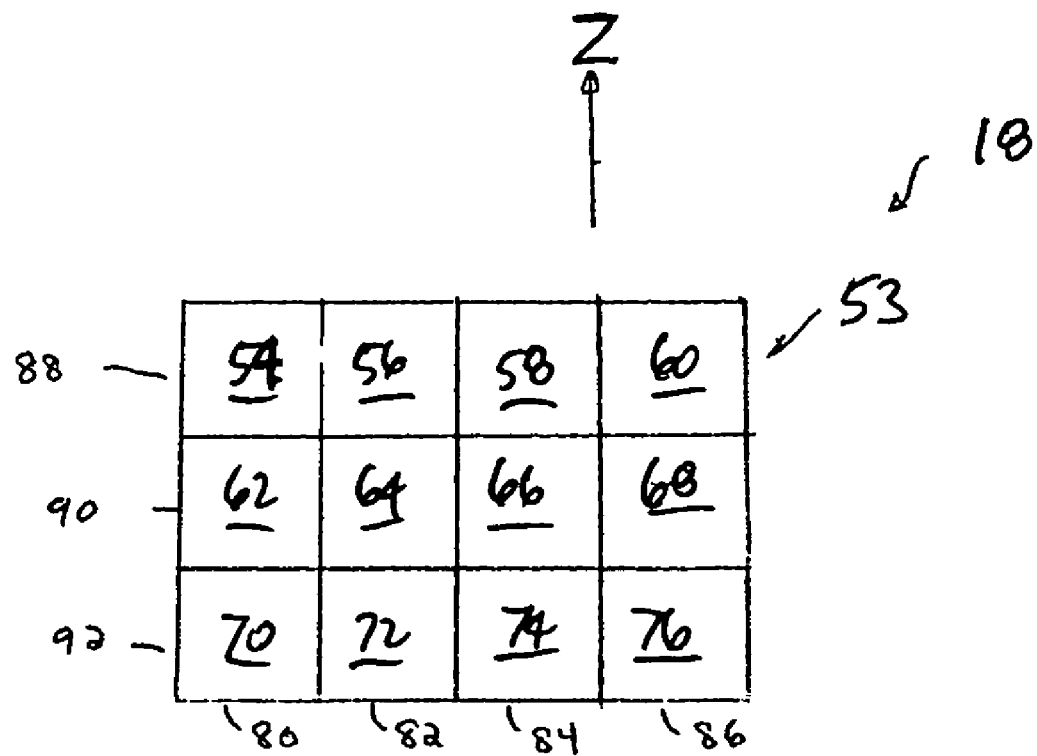
FIG. 4 is a detailed pictorial schematic drawing of a section of the multirow detector array shown in FIG. 3.

Detector array 18 comprises a 2-D array of detector elements 20 arranged in rows and columns. Each row comprises a plurality of detector elements 20 extending generally along an in-slice dimension. Each column comprises a plurality of detector elements extending generally parallel to the z-axis. For example and referring to FIG. 4, an illustrated portion 53 of x-ray detector array 18 includes detector elements 54, 56, 58, 60, 62, 64, 66, 68, 70, 72, 74, and 76. Portion 53 includes columns 80, 82, 84, and 86 and channels 88, 90, and 92. Column 80 includes detector elements 54, 62, and 70. Column 82 includes detector elements 56, 64, and 72. Column 84 includes detector elements 58, 66, and 74. Column 86 includes detector elements 60, 68, and 76. Row 88 includes detector elements 54, 56, 58, and 60. Row 90 includes detector elements 62, 64, 66, and 68. Row 92 includes detector elements 70, 72, 74, and 76. Detector array 18 transmits radiation attenuation signals associated with detector elements to data acquisition system 32.

Some configurations of the present invention reduce image artifacts and noise by imposing a greater consistency on projection data across detector rows. In some configurations of the present invention, this consistency is imposed by requiring an interpolation before a final 3D backprojection. Because the interpolation takes place across detector rows, a thicker image is obtained, and this thicker image is a goal of z-filtering. Thus, a technical effect of some configurations of the present invention is the generation of images of objects (or, in some configurations, electronic representations convertible into visible images) having a relatively thicker image as well as reduced artifacts in comparison to the images produced by known CT imaging systems.

Figure 5:
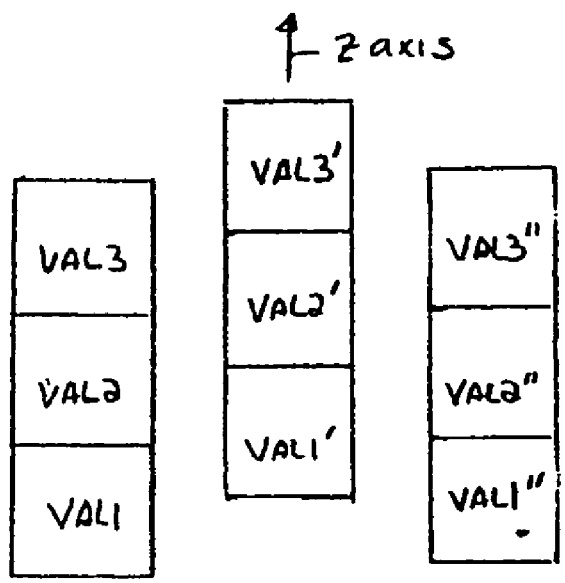
FIG. 5 is a pictorial drawing representative of x-ray attenuation data values associated with a column of detector elements of the detector array in FIG. 4.
Figure 6:
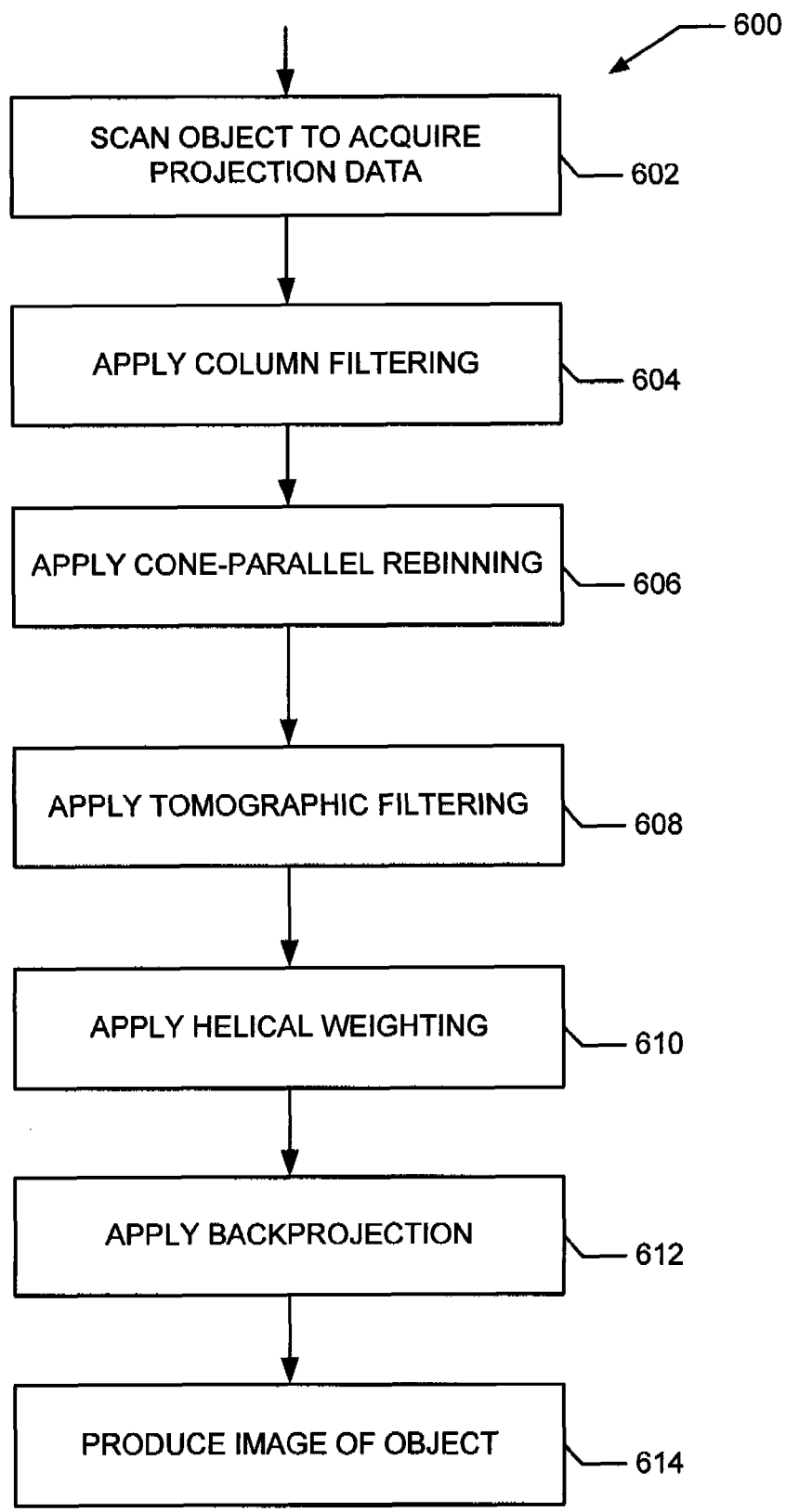
FIG. 6 is a flowchart representative of some configurations of the present invention for generating a cross-section image of an object.

In various configurations of the present invention and referring to flow chart 600 of FIG. 6, a technical effect is achieved by a user first instructing a CT imaging system (for example, imaging system 10) having a detector array 18 with at least two detector rows to initiate a scan of an object 22 to acquire projection data or, synonymously, projection samples at 602. The projection data includes data obtained from at least two rows of the detector. Referring to FIG. 5, some of these samples are indicated as data values VAL1, VAL2, and VAL3, which in this example are associated with a column 80 of detector array 18. In some configurations, data values VAL1, VAL2, and VAL3, as well as any other data values acquired during the scan that are to be used in constructing an image of object 22, are transmitted to DAS 32 for further processing by image reconstructor 34.

For simplicity, and referring again to FIG. 5, only one set of samples in a particular view and a particular detector channel are shown, although the manner in which other rows are treated is the same. Original projection samples, $p(\gamma_i, \beta_m, z_n)$, n=1, ..., N, represented in FIG. 5 by VAL1, VAL2, and VAL3, are interpolated to produce a new set of samples, $p'(\gamma_i, \beta_m, z'_n)$, represented as VAL1', VAL2', and VAL3'. The interpolated samples are then re-interpolated back to the original sample location to produce $p''(\gamma_i, \beta_m, z_n)$, represented as VAL1", VAL2", and VAL3". More specifically, the $p'(\gamma_i, \beta_m, z'_n)$ in some configurations of the present invention is written:

$$p'(\gamma_i, \beta_m, z'_n) = \sum_{k=-K}^{K} f(k) p(\gamma_i, \beta_m, z_{n+k}) \qquad (4)$$

and $p''(\gamma_i, \beta_m, z_n)$ is written:

$$p''(\gamma_i, \beta_m, z_n) = \sum_{k=-K'}^{K'} w(k) p(\gamma_i, \beta_m, z'_{n+k}) \qquad (5)$$

By modifying the interpolation kernel $f$ and w, the amount of shift between $z_n$ and $z'_n$, the noise, slice thickness, and artifact suppression can be changed.

The two interpolation operations (4) and (5) together for a step referred to herein as "column filtering." These two operations can be combined into a single step in some configurations by providing, in essence, a filtering step with an appropriate filtering kernel:

$$p''(\gamma_i, \beta_m, z'_n) = \sum_{k=-K}^{K} f'(k, n) p'(\gamma_i, \beta_m, z_{n+k}). \quad (6)$$

Configurations represented by FIG. 5 keep the detector grid the same by carrying out either the two times of z-interpolation as in equations (4) (5), or the integrated z-interpolation as in equation (6). Thus, in these configurations, the nominal and actual z-sampling rate after z-filtering are the same as those before z-filtering.

In some configurations of the present invention and referring again to FIG. 6, column filtering is applied to projection data at 604. After the column filtering is applied, some (but not all) configurations of the present invention a cone-parallel rebinning of the interpolated data at 606. This is followed in some configurations by tomographic filtering (e.g., applying a ramp filter to the data) at 608. If the data at 602 was acquired in a helical scan, the filtered data is then helically weighted at 610. (Application of helical weighting is not required in all configurations. In some configurations, an explicit decision is made to perform helical weighting dependent upon whether the projection data was acquired in a helical scan. However, some configurations do not include facilities for making such a decision and either always apply helical weighting or do not include facilities for applying helical weighting.) In some configurations of the present invention, the order of the application of tomographic filtering 608 and helical weighting 610 is reversed. Whether the data was helically weighted or not, the next step in some configurations of the present invention is a backprojection step 612 to produce data representative of an image of object 22. The backprojection in various configurations of the present invention is a 3D backprojection. Some configurations of the present invention actually produce an image of object 22 at 614 that is displayed on display device 42 using the data representative of an image.

Figure 7:
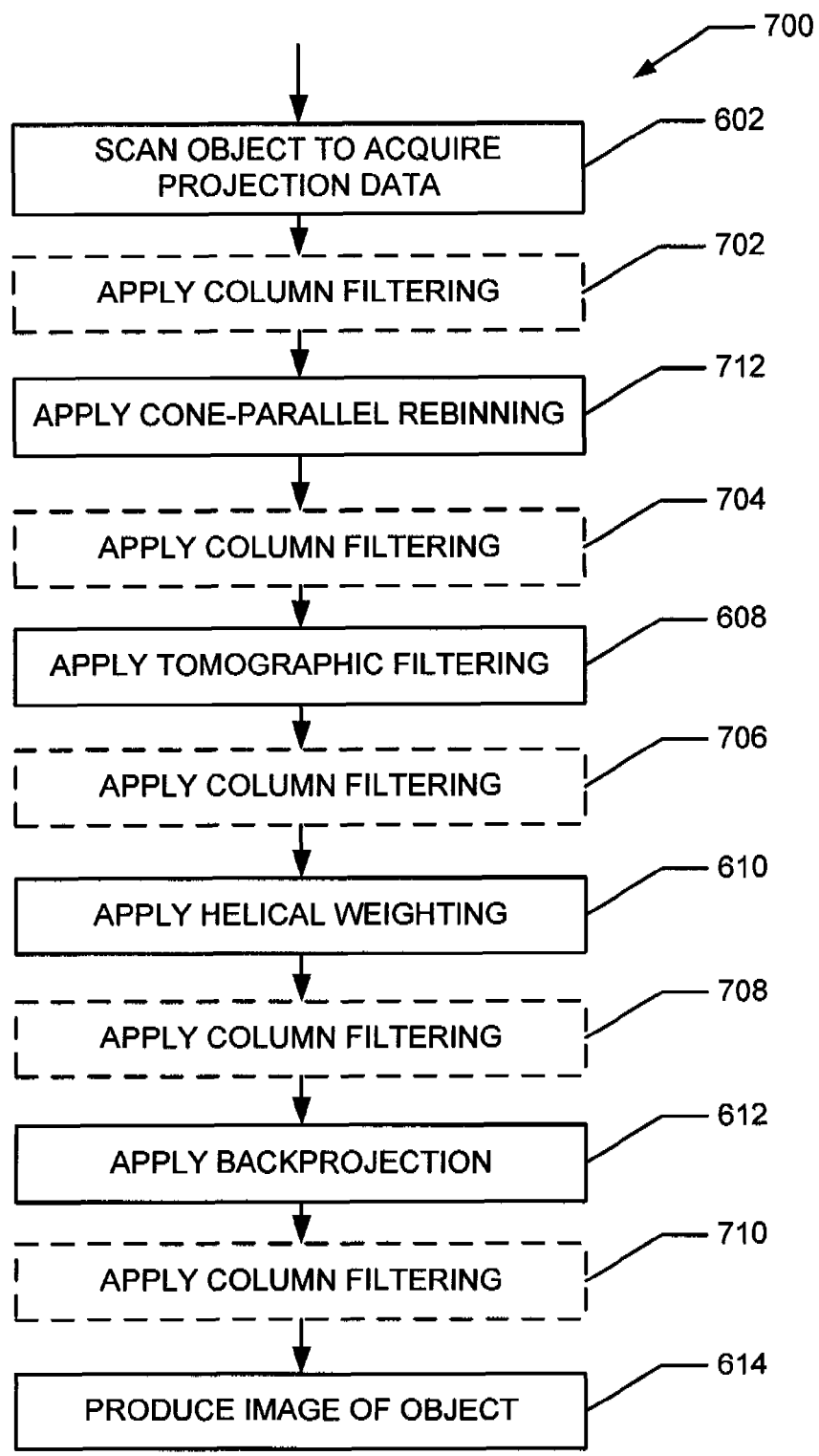
FIG. 7 is a modified, generalized version of the flowchart of FIG. 6 representative of additional configurations of the present invention.
Figure 8:
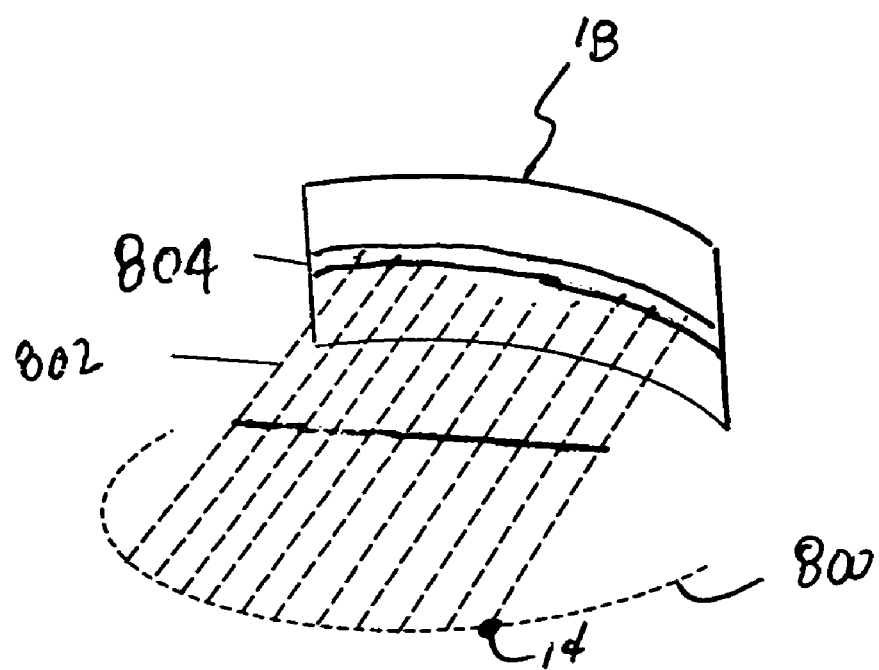
FIG. 8 is a representation of a prior art 3D forward projection, showing how each backprojection path corresponds to an x-ray path that generated a corresponding projection sample.

The ordering of the steps described above is quite flexible, and other configurations of the present invention perform the steps in a different order to produce equivalent results. Referring to the modified flowchart 700 of FIG. 7, the possible locations of flowchart 700 at which column filtering 604 can be applied are indicated at 702, 704, 706, 708, and 710. However, only one column filtering operation is, or need be, performed in any particular configuration of the present invention. Thus, for example, if column filtering at 704 is applied in one configuration, it is not also applied (or need not also be applied) at 702, 706, 708, or 710. Similarly, if column filtering at 706 is applied, it is also not applied (or need not also be applied) at 702, 704, 708, or 710. Also, not all configurations of the present invention apply cone-parallel rebinning at 712, nor do all configurations of the present invention apply helical weighting at 610 (e.g., a helical weighting is not applied if the scan is not a helical scan). Moreover, some configurations of the present invention reverse the order in which helical weighting 610 and tomographic filtering 608 are applied so that the order is the opposite of that shown in FIG. 7. However, the operations shown in FIG. 7 can be viewed as a pipeline operating on acquired projection data. For that reason, a statement such as "applying a helical weighting to the pipelined projection data" is used herein to mean that, in a sequence of operations that starts with projection data and applies various operations to the projection data, wherein each step modifies the data, a helical weighting step is applied. Moreover, a recitation that some specified operations are performed in a particular sequence is not intended to exclude configurations in which additional operations are performed, regardless of whether these additional operations are performed before, after, and/or between the specified operations, or in some combination thereof.

Figure 9:
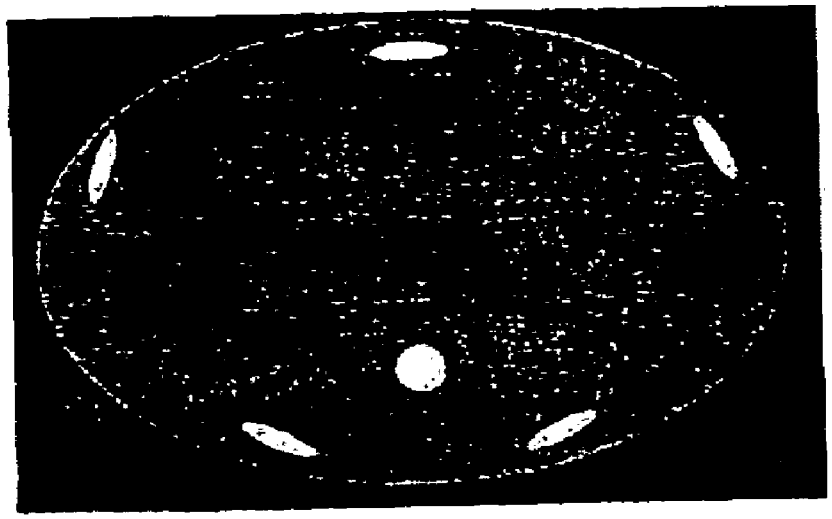
FIG. 9 is an example of a cross-sectional image of a helical body phantom having a distorted artifact region generated by a prior art CT imaging system. Significant artifacts can be seen in the form of ray-like patterns emanating from some of the circular and oval internal features of the phantom.
Figure 10:
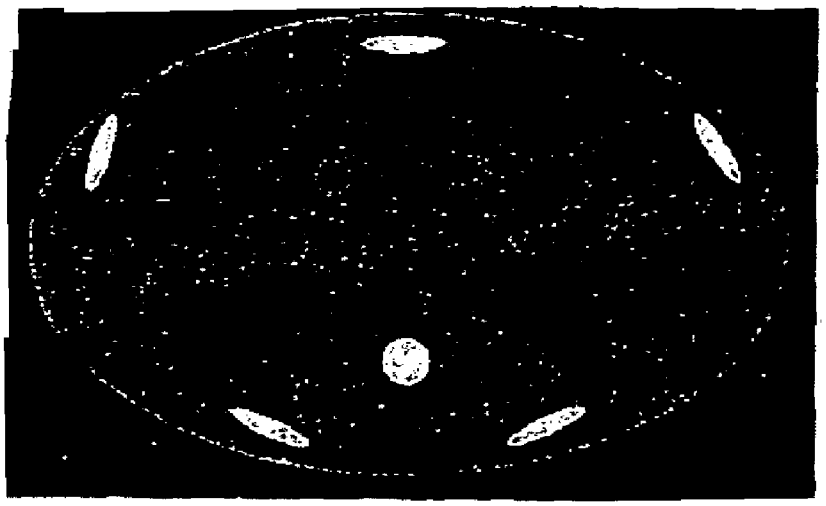
FIG. 10 is an illustration of an improved cross-sectional image of FIG. 8 obtained in some configurations of the present invention.

Referring to FIG. 10, a reconstructed image is shown with linear interpolation and $z'_n$ selected at the mid-point of the original projection. The image of FIG. 10 corresponds to the image of FIG. 9, the latter being reconstructed without utilizing a configuration of the present invention. Noise in the image reconstructed in FIG. 10 was found to be reduced from 11.3 HU to 8.5 HU relative to that of FIG. 9. It will be appreciated that thick image slices produced using configurations of the present invention thus have reduced noise.

Figure 11:
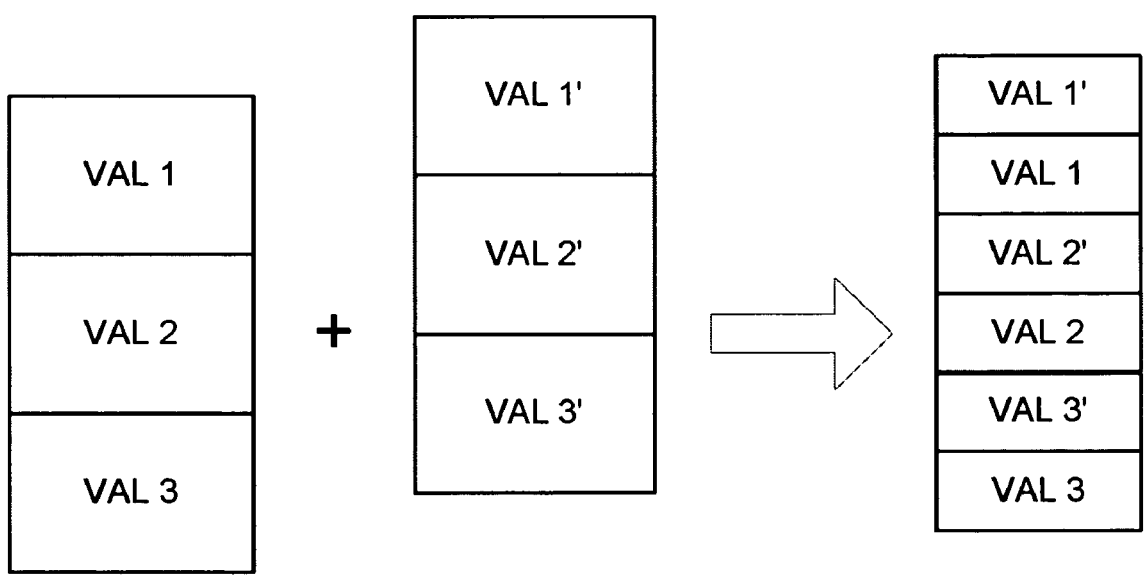
FIG. 11 is a pictorial drawing representative of another set of x-ray attenuation data values associated with a column of detector elements of the detector array in FIG. 4. The configuration represent in FIG. 11 differs from that in FIG. 5 because it realizes an up-sampling along a z-direction by combining original projection samples with and shifted interpolated projection samples.

In yet another configuration of the present invention and referring to FIG. 11, shifted and interpolated projection samples are used. These samples can be written:

$$p'(\gamma_i, \beta_m, z_n) = \sum_{k=-1,1}^{k \neq 0} f_i(k, n) p(\gamma_i, \beta_m, z_{n+k}) \quad (7)$$

where $f_i(k, n)$ represents the kernel of an inter-row interpolation kernel, in which only two adjacent original rows are involved in the generation of a new row between these two adjacent rows. Supposing that the z-dimension of the original projection samples is N, the z-dimension of the combined projection samples becomes 2N−1, and the combination process can be written:

$$p''(\gamma_i, \beta_m, z_n) = \quad (8)$$
$$\begin{cases} p(\gamma_i, \beta_m, z_n) & \text{while} \quad n = 0, 2, 4, \ldots 2N-1 \\ p'(\gamma_i, \beta_m, z_n) & \text{while} \quad n = 1, 3, 5, \ldots, 2N-2 \end{cases}$$

In these configurations, the actual z-sampling rate of combined projection samples remains the same, but the nominal z-sampling rate is doubled because of the combination process. Based on the combined projection samples, a z-filtering is carried out in accordance with an expression written as:

$$p'''(\gamma_i, \beta_m, z'_n) = \sum_{k=-K}^{K} w(k, n) p''(\gamma_i, \beta_m, z_{n+k}) \quad (9)$$

In some configurations of the present invention, a CT imaging apparatus is used, as are the image processing and computing facilities therein. However, projection data can also be processed and images created on stand-alone workstations. For example, in some configurations, projection data acquired on a CT imaging apparatus is processed on a stand-alone workstation or computer by transferring the projection data to the workstation or computer and by running firmware and/or software program(s). In some configurations, the program or programs are embodied on one or more media, such as a CD-ROM, CD-R, CD-RW, DVD, floppy diskette, memory card, ROM, etc. (hereinafter, "a machine readable medium or media") having machine-readable instructions recorded thereon that are configured to instruct a processor or processors of the workstation or computer to perform steps described above. For example, the instructions can include instructions to input projection data of an object, and to reconstruct data representative of an image of an object utilizing the projection data wherein instructions for the reconstruction include instructions for pipelining the projection data through a pipeline of operations including column filtering, tomographic filtering, and backprojection.

Machine-readable instructions can be divided arbitrarily across media, or even different types of media. Therefore, the phrase "a machine readable medium having machine-readable instructions recorded thereon" is intended to encompass not only configurations in which instructions are recorded on a single medium, but also configurations in which the instructions are recorded on a plurality of media, which may include different types of media. Furthermore, the term "recorded thereon" is not meant to be read literally as being recorded on the surface thereof, but rather is intended to encompass without limitation (unless otherwise explicitly limited) all methods of machine recording, so as not to exclude, for example, magnetic recording (such as floppy diskettes or hard disk drives), pitting and embedding (such as on a CD-ROM), burning (either of dyes, such as on CD-R, or of chips, such as ROMs and flash memory), etc.

While the invention has been described in terms of various specific embodiments, those skilled in the art will recognize that the invention can be practiced with modification within the spirit and scope of the claims.

What is claimed is:

1. A method for obtaining data, said method comprising:
   scanning an object using a CT imaging system having at least two detector rows to acquire projection data, wherein the projection data includes at least some data obtained from at least two rows of the detector array;
   reconstructing data representative of an image of the object utilizing the projection data, wherein said reconstruction includes pipelining the acquired projection data through a z-filtering pipeline of operations including column-filtering, tomographic filtering, and backprojection, wherein the column-filtering comprises a first interpolation operation comprising a first interpolation kernel and a second interpolation operation comprising a second interpolation kernel wherein the second interpolation kernel produces an equal but opposite data shift as the first interpolation kernel and wherein modifying at least one of the first and second interpolation kernels changes an amount of noise, slice thickness, and artifact suppression between an original sample and an interpolated sample; and
   outputting the reconstructed data to a display device.

2. A method in accordance with claim 1 further comprising producing an image of the object utilizing the data representative of the image of the object.

3. A method in accordance with claim 1 wherein said reconstructing data representative of an image of the object comprises applying column filtering, tomographic filtering and backprojecting to the pipelined projection data, in that order.

4. A method in accordance with claim 1 wherein said reconstructing data representative of an image of the object comprises applying tomographic filtering, column filtering, and backprojecting to the pipelined projection data, in that order.

5. A method in accordance with claim 1 wherein said reconstructing data representative of an image of the object comprises applying tomographic filtering, backprojecting, and column filtering to the pipelined projection data, in that order.

6. A method in accordance with claim 1 wherein said reconstructing data representative of an image of the object further comprises applying a cone-parallel rebinning to the pipelined projection data.

7. A method in accordance with claim 1 wherein said reconstructing data representative of an image of the object further comprises applying a helical weighting to the pipelined projection data.

8. A CT imaging apparatus comprising:
   a detector array having at least two rows and a plurality of columns;
   a radiation source configured to project a beam of radiation through an object to be imaged onto the detector array; and
   a computer system configured to:
   scan an object to acquire projection data, wherein the projection data includes at least some data obtained from at least two rows of the detector array; and
   reconstruct data representative an image of the object utilizing the projection data, wherein said reconstruction includes pipelining the acquired projection data through a z-filtering pipeline of operations including column-filtering, tomographic filtering, and backprojection, wherein the column-filtering comprises a first interpolation operation comprising a first interpolation kernel and a second interpolation operation comprising a second interpolation kernel wherein the second interpolation kernel produces an equal but opposite data shift as the first interpolation kernel and wherein modifying at least one of the first and second interpolation kernels changes an amount of noise, slice thickness, and artifact suppression between an original sample and an interpolated sample.

9. An apparatus in accordance with claim 8 further having a display screen and further configured to produce an image of the object on the display screen utilizing the data representative of the image of the object.

10. An apparatus in accordance with claim 8 wherein to reconstruct data representative of an image of the object, said apparatus configured to apply column filtering, tomographic filtering and backprojecting to the pipelined projection data, in that order.

11. An apparatus in accordance with claim 8 wherein to reconstruct data representative of an image of the object, said apparatus configured to apply tomographic filtering, column filtering, and backprojecting to the pipelined projection data, in that order.

12. An apparatus in accordance with claim 8 wherein to reconstruct data representative of an image of the object, said apparatus configured to apply tomographic filtering, backprojecting, and column filtering to the pipelined projection data, in that order.

13. An apparatus in accordance with claim 8 wherein to reconstruct data representative of an image of the object, said apparatus further configured to apply a cone-parallel rebinning to the pipelined projection data.

14. An apparatus in accordance with claim 8 wherein to reconstruct data representative of an image of the object, said apparatus further configured to apply a helical weighting to the pipelined projection data.

15. A computer readable medium having recorded thereon machine-readable instructions configured to instruct a processor to:
input projection data;
reconstruct data representative of an image of the object utilizing the projection data, wherein said reconstruction includes instructions to pipeline the acquired projection data through a z-filtering pipeline of operations including column-filtering, tomographic filtering, and backprojection, wherein the column-filtering comprises a first interpolation operation comprising a first interpolation kernel and a second interpolation operation comprising a second interpolation kernel wherein the second interpolation kernel produces an equal but opposite data shift as the first interpolation kernel and wherein modifying at least one of the first and second interpolation kernels changes an amount of noise, slice thickness, and artifact suppression between an original sample and an interpolated sample; and
produce an image of the object on a display screen utilizing the data representative of the image of the object.

16. A medium in accordance with claim 15 wherein to reconstruct data representative of an image of the object, said instructions further include instructions configured to apply column filtering, tomographic filtering and backprojecting to the pipelined projection data, in that order.

17. A medium in accordance with claim 15 wherein to reconstruct data representative of an image of the object, said instructions further include instructions configured to apply tomographic filtering, column filtering, and backprojecting to the pipelined projection data, in that order.

18. A medium in accordance with claim 15 wherein to reconstruct data representative of an image of the object, said instructions further include instructions configured to apply tomographic filtering, backprojecting, and column filtering to the pipelined projection data, in that order.

19. A medium in accordance with claim 15 wherein to reconstruct data representative of an image of the object, said instructions further include instructions configured to apply a cone-parallel rebinning to the pipelined projection data.

20. A medium in accordance with claim 15 wherein to reconstruct data representative of an image of the object, said instructions further include instructions configured to apply a helical weighting to the pipelined projection data.

* * * * *